United States Patent
Sartor et al.

(10) Patent No.: US 10,470,704 B2
(45) Date of Patent: Nov. 12, 2019

(54) SYSTEM AND METHOD FOR ESTIMATING CARDIOVASCULAR FITNESS OF A PERSON

(71) Applicant: KONINKLIJKE PHILIPS N.V., Eindhoven (NL)

(72) Inventors: Francesco Sartor, Eindhoven (NL); Alberto Giovanni Bonomi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 164 days.

(21) Appl. No.: 14/915,914

(22) PCT Filed: Sep. 3, 2014

(86) PCT No.: PCT/EP2014/068642
§ 371 (c)(1),
(2) Date: Mar. 2, 2016

(87) PCT Pub. No.: WO2015/036289
PCT Pub. Date: Mar. 19, 2015

(65) Prior Publication Data
US 2016/0206248 A1    Jul. 21, 2016

(30) Foreign Application Priority Data
Sep. 16, 2013 (EP) .................................. 13184505

(51) Int. Cl.
*A61B 5/00* (2006.01)
*A61B 5/024* (2006.01)
(Continued)

(52) U.S. Cl.
CPC .......... *A61B 5/4866* (2013.01); *A61B 5/0205* (2013.01); *A61B 5/02438* (2013.01);
(Continued)

(58) Field of Classification Search
CPC ..... A61B 5/1118; A61B 5/4866; A61B 5/681; A61B 5/0205; A61B 5/7264;
(Continued)

(56) References Cited

U.S. PATENT DOCUMENTS 4,566,461 A * 1/1986 Lubell .................... A61B 5/024
377/24.2
4,898,182 A * 2/1990 Hawkins ................ A61B 5/222
600/509

(Continued)

FOREIGN PATENT DOCUMENTS

CN      1833603 A      9/2006
CN     102138789 A     8/2011
(Continued)

OTHER PUBLICATIONS

American College of Sports Medicine. "Metabolic Equations for Gross VO2 in Metric Units." Mar. 2, 2013.*

(Continued)

*Primary Examiner* — Meredith Weare (57) ABSTRACT

The present invention relates to a system (1) for estimating cardiovascular fitness of a person, comprising a heart rate monitor (10) for acquiring a heart rate signal including information about the heart rate of the person, an activity monitor (20) for acquiring an activity signal indicative of physical activity of the person, a classifier (30) for classifying the activity of the person based on the acquired activity signal, a selector (40) for selecting one or more heart rate features obtained from the acquired heart rate signal based on the acquired heart rate signal and the classification of the activity for use in an estimation of the cardiovascular fitness of the person, and an estimator (50) for estimating the cardiovascular fitness of the person based on the one or more selected heart rate features.

20 Claims, 3 Drawing Sheets

(51) Int. Cl.
*A61B 5/11* (2006.01)
*A61B 5/0205* (2006.01)
*A61B 5/145* (2006.01)

(52) U.S. Cl.
CPC ............ *A61B 5/1118* (2013.01); *A61B 5/681* (2013.01); *A61B 5/7264* (2013.01); *A61B 5/02405* (2013.01); *A61B 5/02416* (2013.01); *A61B 5/1123* (2013.01); *A61B 5/14542* (2013.01); *A61B 5/7246* (2013.01); *A61B 2505/09* (2013.01); *A61B 2562/0219* (2013.01)

(58) Field of Classification Search
CPC ............ A61B 2505/09; A61B 5/02438; A61B 5/14542; A61B 5/02405; A61B 5/02416; A61B 5/1123; A61B 5/7246; A61B 2562/0219

See application file for complete search history.

(56) References Cited

U.S. PATENT DOCUMENTS

| | | | |
|---|---|---|---|
| 6,135,951 A | 10/2000 | Richardson | |
| 6,241,684 B1 | 6/2001 | Amano | |
| 6,436,052 B1 | 8/2002 | Nikolic | |
| 9,433,372 B2* | 9/2016 | Russell | G06F 19/3406 |
| 2005/0256545 A1* | 11/2005 | Koh | A61B 5/0031 607/17 |
| 2007/0249949 A1* | 10/2007 | Hadley | A61B 5/024 600/519 |
| 2008/0161653 A1* | 7/2008 | Lin | A61B 5/0833 600/300 |
| 2010/0249619 A1* | 9/2010 | Kasama | A61B 5/02416 600/502 |
| 2011/0021319 A1* | 1/2011 | Nissila | A61B 5/222 482/8 |
| 2011/0152695 A1* | 6/2011 | Granqvist | A61B 5/0006 600/481 |
| 2012/0029370 A1* | 2/2012 | Rocker | A61B 5/024 600/508 |
| 2012/0108991 A1* | 5/2012 | Song | A61B 5/0245 600/509 |
| 2013/0023739 A1* | 1/2013 | Russell | G06F 19/3406 600/301 |
| 2013/0290359 A1* | 10/2013 | Eronen | G06F 17/30 707/758 |
| 2014/0088378 A1* | 3/2014 | Muzet | A61B 5/02125 600/301 |
| 2014/0088444 A1* | 3/2014 | Saalasti | A61B 5/0205 600/484 |
| 2014/0107493 A1* | 4/2014 | Yuen | H04W 4/027 600/473 |
| 2014/0213858 A1* | 7/2014 | Presura | A61B 5/721 600/301 |
| 2014/0276127 A1* | 9/2014 | Ferdosi | A61B 5/0245 600/483 |

FOREIGN PATENT DOCUMENTS

| | | |
|---|---|---|
| EP | 2335563 A1 | 6/2011 |
| EP | 2524647 A1 | 11/2012 |
| FR | 2576205 A3 | 7/1986 |
| JP | 2007160076 A | 6/2007 |
| JP | 2012235920 A | 12/2012 |
| WO | 2012057852 A1 | 5/2012 |
| WO | 2013038296 A1 | 3/2013 |
| WO | 2013076656 A1 | 5/2013 |

OTHER PUBLICATIONS

Altini, Marco et al "Personalizing Energy Expenditure Estimation using a Cardiorespiratory Fitness Predicate", 7th International Conf. on Pervasive Computing Technologies for Healthcare (Pervasive Health) May 2013, pp. 65-72.

Bassett, Dr et al Limiting Factors for Maximum Oxygen Uptake and Determinnats of Endurance Performance, Med Sci Sports Exerc. Jan. 2000, vol. 32, No. 1, pp. 70-84.

Preece, Stephen J. et al "Acitvity Identification using Body-Mounted Sensors—a Review of Classificaiton Techniques", Physiological Measurement, vol. 30, No. 4, 2009.

* cited by examiner

SYSTEM AND METHOD FOR ESTIMATING CARDIOVASCULAR FITNESS OF A PERSON

CROSS-REFERENCE TO PRIOR APPLICATIONS

This application is the U.S. National Phase application under 35 U.S.C. § 371 of International Application No. PCT/EP2014/068642, filed on Sep. 3, 2014, which claims the benefit of European Patent Application No. 13184505.9, filed on Sep. 16, 2013. These applications are hereby incorporated by reference herein.

FIELD OF THE INVENTION

The present invention relates to a system, a method, a processor and a processing method for estimating cardiovascular fitness of a person. Further, the present invention relates to a computer program for implementing said processing method.

BACKGROUND OF THE INVENTION

Cardiovascular fitness is important in several fields, such as sports, fitness industry, clinical for diagnostic, prognostic and rehabilitation, and self monitoring in asymptomatic individuals. The direct measurement of fitness requires maximal physiological effort, which is associated with a greater risk of cardiovascular events, expensive devices and trained personnel. The indirect estimation of fitness overcomes some of these limitations but still requires to undergo rigorously a specific protocol, takes time and often involves the use of specific equipment (such as lab-bicycles, steps etc.).

U.S. Pat. No. 6,241,684 discloses a device, which is capable of determining the maximum oxygen uptake quantity without the restriction of a large device or requiring troublesome operations to be carried out. The device displays the upper and lower limit values for the pulse rate corresponding to an appropriate exercise intensity, and realizes in a wireless manner by means of optical communications the sending and receiving of information such as pulse wave signals to and from an information processing device which processes pulse wave information. The device is provided with a pulse wave detector for detecting the test subject's pulse waveform; an FFT processor for determining the test subject's heartbeat rate from the pulse waveform; a body motion detector for detecting body motion when the test subject is running; an FFT processor for determining the pitch from body motion during running by the test subject; exercise intensity calculator for determining pitch, the test subject's stride, and the exercise intensity from body motion during running; and a nomogram recorder for recording the relationship indicated by an Astrand-Ryhming nomogram, and determining the maximum oxygen uptake quantity from the heart rate and exercise intensity. The obtained maximum oxygen uptake quantity is divided by the test subject s body weight, to calculate the maximum oxygen uptake quantity per unit body weight. Next, the maximum oxygen uptake quantity and pulse according to sex are determined, and the pulse rate is multiplied by the upper and lower limit value coefficients, to determine the upper limit value and the lower limit value for the pulse rate.

WO 2012/057852 A1 discloses techniques for detecting ischemia and classifying a type of ischemia. Electrograms of cardiac activity are generated and evaluated. Ischemia is detected and classified as benign or malignant based on whether a change of an electrogram metric is detected, or first detected, in an electrogram. The relative timing of the change in the electrogram metric and a change in heart rate or patient activity may also be considered. The system may create a stress test for detecting ischemia by instructing the patient to exercise or increasing the cardiac pacing rate.

EP 2 524 647 A1 discloses a system and method for determining sleep stages of a person. A heart rate and a body movement are detected and classified. Combinations of heart rate class and body movement class are identified and a sleep stage and/or a sleep event of the person is determined based thereon.

EP 2 335 563 A1 discloses a system for processing exercise-related data comprising heart activity sensor and a motion sensor further. The type of exercise the user wishes to carry out is input by the user through a user interface. Based thereon exercise-related information can be calculated.

Altini et al. disclose personalizing energy expenditure estimation using a heart rate normalization factor in order to reduce an energy estimation error and inter-individual variability ("Personalizing energy expenditure estimation using a cardiorespiratory fitness predicate," 7th International Conference on Pervasive Computing Technologies for Healthcare (PervasiveHealth), pp. 65-72, 5-8 May 2013). The estimation of said normalization factor is based on a fixed set of parameters comprising the subject's heart rate while lying down resting and walking at different speeds together with anthropometric characteristics.

SUMMARY OF THE INVENTION

It is an object of the present invention to provide a system, a method, a processor and a processing method for estimating cardiovascular fitness of a person which do not require the user to rigorously follow a predetermined protocol and/or to use a certain equipment like a treadmill or ergometer, but allows the user to reliably assess his cardiovascular fitness in everyday life situations.

In a first aspect of the present invention a system for estimating cardiovascular fitness of a person is presented comprising a heart rate monitor for acquiring a heart rate signal including information about the heart rate of the person, an activity monitor for acquiring an activity signal indicative of physical activity of the person, a classifier for classifying the activity of the person based on the acquired activity signal, a selector for selecting one or more heart rate features obtained from the acquired heart rate signal based on the acquired heart rate signal and the classification of the activity for use in an estimation of the cardiovascular fitness of the person, and an estimator for estimating the cardiovascular fitness of the person based on the one or more selected heart rate features.

In a further aspect of the present invention a processor for estimating cardiovascular fitness of a person is presented comprising processing means configured to classify the activity of the person based on an acquired activity signal indicative of physical activity of the person, select one or more heart rate features obtained from an acquired heart rate signal including information about the heart rate of the person based on the acquired heart rate signal and the classification of the activity for use in an estimation of the cardiovascular fitness of the person, and estimate the cardiovascular fitness of the person based on the one or more selected heart rate features.

In yet further aspects of the present invention, there are provided corresponding methods, a computer program which comprises program code means for causing a computer to perform the steps of the processing method disclosed herein when said computer program is carried out on a computer as well as a non-transitory computer-readable recording medium that stores therein a computer program product, which, when executed by a processor, causes the processing method disclosed herein to be performed.

Preferred embodiments of the invention are defined in the dependent claims. It shall be understood that the claimed methods, processor, computer program and medium have similar and/or identical preferred embodiments as the claimed system and as defined in the dependent claims.

The present invention is based on the idea to assess ("estimate") the cardiovascular fitness of a person (user) without asking the person to undergo any specific protocol. By monitoring the user's heart rate (HR) and physical activity the type of activity performed by the person is recognized ("classified"), and mainly based on this recognition it is decided which HR features to use in order to assess the person's fitness. Further, information about which HR phase is currently available is used for selecting the most appropriate HR features for estimating the person's fitness. Thus, the problem that the person needs to rigorously follow a predetermined protocol which is time consuming and in several cases requires specific equipment (such as a stairmaster, treadmill or ergometer) is overcome. The present invention allows an accurate estimation of the person's cardiovascular fitness in everyday life situations.

Generally, various kinds of activity monitors may be used for acquiring an activity signal indicative of the person's physical activity. Preferably, an activity pattern including e.g. an activity count (number of movements per unit time), the intensity of the activity, the acceleration of the moved body part, etc. is obtained. In a preferred embodiment said activity monitor includes an accelerometer for acquiring an acceleration signal indicative of acceleration of at least part of the body of the person as activity signal. Such accelerators are widely known, inexpensive and can be easily worn by the person without hampering the person's mobility.

According to another embodiment said classifier is configured to classify the activity of the person at least into activity and no activity, in particular into cycling, walking, running, raising, steady recovery and no activity. The better the type of activity can be classified, the more appropriately the HR features can be selected for fitness assessment. Preferably, one or more regression models are applied and various parameters obtained from the activity signal are used for this classification.

In an embodiment said selector is configured to select one or more heart rate features from the group of heart rate features comprising heart rate recovery, peak heart rate, heart rate variability, heart rate rise, resting heart rate.

Preferably, said selector is configured to select one or more heart rate features based on which heart rate phase is currently present. For instance, in case of rising HR different HR features (e.g. slope, linear intercept) are preferably used than in case of HR recovery (HR features used then are e.g. time constant over first 10 seconds, linear intercept).

The estimator is advantageously configured to estimate the maximum oxygen uptake indicating the physical fitness of the person. The cardiovascular function is ascribable to the maximal cardiac output, which, via the generally known Fick's principle, is related to maximal oxygen uptake ($VO_2$max), as e.g. described in Bassett D R, Jr., Howley E T, Limiting factors for maximum oxygen uptake and determinants of endurance performance, Med Sci Sports Exerc. 2000 January; 32(1):70-84.

In still another embodiment the system further comprises an interface for receiving user information about the person including one or more age, gender, weight, height, body mass index of the person. Further, said estimator is configured to estimate the cardiovascular fitness of the person based on the one or more selected heart rate features and the user information in this embodiment. This further increases the accuracy of the fitness estimation. The cardiovascular fitness is preferably computed considering the mean $VO_2$max estimated by each heart rate feature weighted for the relative error assessed in the laboratory.

Preferably, said selector is configured to select as heart rate features one or more heart rate features derived from a peak heart rate if physical activity of the person is detected, one or more heart rate recovery parameters if no physical activity of the person is detected, and/or one or more heart rate statistical measurements if no physical activity of the person is detected and if the heart rate of the person is at rest.

This embodiment has shown to provide reliable and accurate results of the fitness estimation.

Further, in an embodiment directed to even further increase the accuracy, said estimator is configured to evaluate the consistency between the cardiovascular fitness estimated based on the different selected heart rate features, in particular by use of a root mean square estimation.

In more practical embodiments said heart rate monitor includes a photo-plethysmography or optical sensor (as e.g. described in WO 2013/076656 A1), and/or said heart rate monitor and said activity monitor are integrated into a common wearable device that can be worn by the person, in particular a wrist worn device (as e.g. described in WO 2013/038296 A1).

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Assessment of the functional capacity of the cardiovascular system is essential in sports medicine. Cardiovascular function is ascribable to the maximal cardiac output, which, via Fick's principle, is related to maximal oxygen uptake ($VO_2$max). In athletes, the $VO_2$max provides valuable information about their aerobic power. Aerobic power is a fundamental determinant of endurance sport performance and an indicator of training efficacy. In the clinical setting, the VO$_2$max provides key diagnostic and prognostic information in several clinical populations, such as patients with coronary artery disease or heart failure. Likewise, cardiovascular function assessment can be very important to evaluate fitness in asymptomatic adults. Although direct determination of VO$_2$max is the most accurate method, it requires a maximal level of exertion by the subject, which brings a higher risk of adverse events in individuals with intermediate to high risk of cardiovascular problems. Moreover, a respiratory gas analysis system is needed, which requires expertise and involves additional costs. Estimation of VO$_2$max during submaximal exercise testing can offer a precious alternative. Over the past decades many protocols have been developed for this purpose. However, submaximal protocols require that the user follows a standardized exercise protocol. In many cases these exercise protocols require time (3 to 6 min) and special pieces of equipment (step, treadmill, ergometers), and above all, users have to follow the instructions properly in order to have a good estimation of their cardiovascular function.

Ultimately, cardiovascular fitness is intrinsically linked to the heart size. A big heart has a greater stroke volume (L/beat). The stroke volume is the volume of blood pumped at each heart cycle (beat). Since the body requires an adequate blood supply, around 5 L/min (in standard subject at rest), the heart rate is adapted according to the stroke volume. If the stroke volume is large, for example 125 mL/beat, then a heart rate (HR) of 40 beat/min would be sufficient to deliver 5 L/min in output. Conversely, if in the same standard subject the heart is smaller, consequently the stroke volume is lesser, for instance 56 mL, then a higher HR of 90 (beat/min) is required to supply the same cardiac output of 5 L/min. This would be true also for exercising conditions and recovery conditions. This is why the HR is often used to assess cardiovascular fitness.

Although resting HR per se is very representative of the fitness level of an individual, this is also affected by external or internal stressors, such as emotions, temperature, digestion, drugs (caffeine) etc. When a person (also called user hereinafter) engages in a physical activity the HR becomes less influenced by these factors and directly related to the metabolic need (VO$_2$) of the activity itself. However, also exercise HR can be influenced by some fitness independent factors such as fatigue, temperature and exercise intensity. Furthermore, if peak exercise HR is close to the maximal HR achievable this will be mainly influenced by age regardless the individual's fitness. The beat to beat variability of the HR (HRV) can be used to predict fitness as well. However, its relation with fitness is less intuitive than the one with just HR. This relationship seems to be in the role that the autonomic nervous system plays in regulating the pace maker of the heart, which as just described is strongly influenced by the heart size. HRV has also some limitations; in fact, it is influenced by respiration, movement and many other factors.

Based on recognitions derived from the above, the inventors have arrived at the rationale to use an integrated approach where these HR derived parameters are used when their prediction power is at their highest. Moreover, accelerometry (or, more generally, detection of the physical activity of the person) is used to classify the type of physical activity, in particular to estimate the workload (speed) of a physical activity. It has been found that this is a valuable information since per each workload (i.e. running speed) a fit/unfit person—given some personal data such as bodyweight, age and gender—should present a somewhat known exercise HR and recovery HR. Therefore, by comparing the measured HR with a reference HR per that estimated workload, the user's actual fitness can be predicted. This additional feature which implies accurate physical activity onset and end recognition and precise activity classification vastly improves the accuracy of the fitness prediction. Details will be explained now in more detail.

Figure 1:
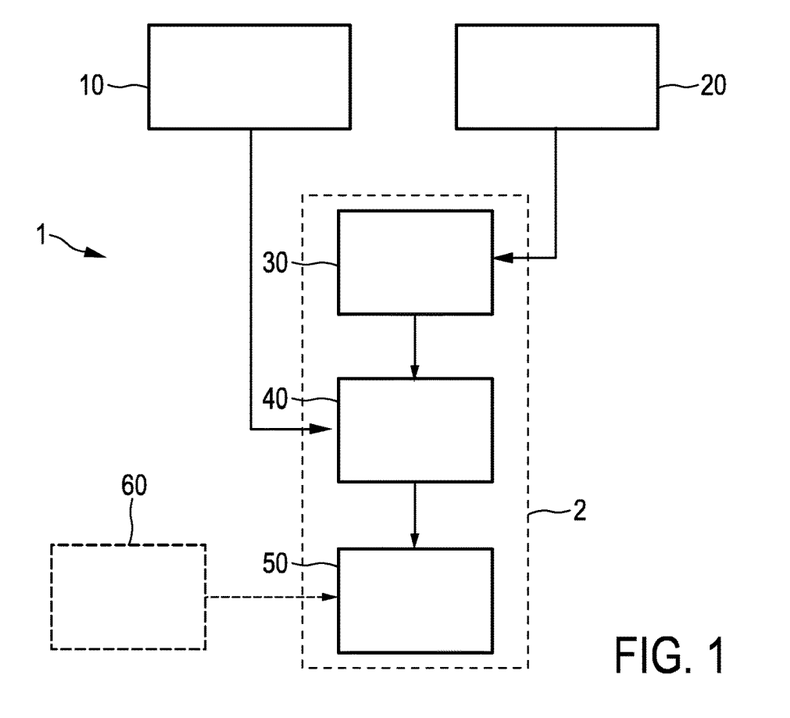
FIG. 1 shows a schematic diagram of an embodiment of a system according to the present invention.

FIG. 1 shows a schematic diagram of an embodiment of a system 1 for estimating cardiovascular fitness of a person according to the present invention. The system 1 comprises a heart rate monitor 10 for acquiring a heart rate signal including information about the heart rate of the person and an activity monitor 20 for acquiring an activity signal indicative of physical activity of the person. A classifier 30 is provided for classifying the activity of the person based on the acquired activity signal. A selector 40 is provided for selecting one or more heart rate features obtained from the acquired heart rate signal based on the acquired heart rate signal and the classification of the activity for use in an estimation of the cardiovascular fitness of the person. An estimator 50 is provided for estimating the cardiovascular fitness of the person based on the one or more selected heart rate features.

In an embodiment the classifier 30, the selector 40 and the estimator 50 are implemented on a processor 2, but other implementations (e.g. through separate processors, software elements, dedicated hardware elements) are possible as well.

Optionally, an interface 60 for receiving user information about the person including one or more age, gender, weight, height, body mass index of the person is additionally provided. Said information may be input by the person, or may be stored in a storage element (not shown). With this option, the estimator 50 is configured to estimate the cardiovascular fitness of the person based on the one or more selected heart rate features and the user information. An example estimation may be:

VO$_2$max=$a0 \times$age+$a1 \times$gender(1 for males,0 for females)+$a3 \times$weight+$a4 \times$height+$a5 \times$BMI+$a6$ HR feature wherein a0 to a6 are predetermined weighting coefficients for assigning weights to the various pieces of information about the person indicating how important the respective pieces of information shall be taken into account in the estimation.

The problem in cardiovascular function (VO$_2$max) that the users need to follow a determined protocol, which is time consuming and in several cases requires specific equipment (step, treadmill, ergometer), and that the exercise protocol has to be followed rigorously in order to allow an accurate estimation of VO$_2$max is overcome by the proposed system. The present invention combines one or more different HR features, such as HR recovery (rate at which the heart rate returns to baseline after a period of exercise), peak HR (maximum HR; highest heart rate the person achieves during the physical activity), HR variability (HRV; variation in the time interval between heartbeats), HR rest (heart rate at rest) according to context and the behaviour of the user. The system decides when to use which HR feature (for example, if the user is sitting or lying, HRV is preferably used; if the user is recovering from an exercise, the HR recovery is preferably used) to reliably assess fitness in free-living conditions.

Figure 2:
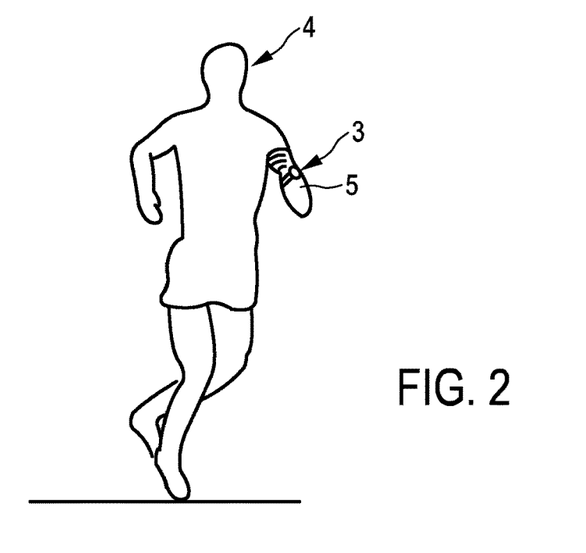
FIG. 2 shows an embodiment of a practical implementation of a system according to the present invention.

Generally, any HR monitor can be used in combination with an activity monitor (e.g. an accelerometer). An example of an integrated device which can be used for this purpose is an optical HR sensor containing a photo-plethysmography sensor (for HR detection) and a 3-axial accelerometer (for activity detection) as e.g. described in WO 2013/038296 A1. Such an integrated device may be implemented as a wrist worn device 3 as exemplarily shown in FIG. 2, which can be worn by a user 4 at his arm 5. This technology allows monitoring HR unobtrusively and comfortably at any location on the body (for example at the wrist). This embodiment is ideal since users will have their fitness evaluation done just by wearing a watch or bracelet throughout the day and possibly night.

Generally, other kinds of HR monitors and physical activity monitors can be used in a system according to the present invention as well. For instance, as HR monitor an ECG sensor or a conventional HR sensor may be used, and as physical activity monitor one or more motion sensors may be used. Other examples of heart rate monitors are PPG sensors, and camera PPG sensors and GPS can be also used as an activity monitor.

Figure 3:
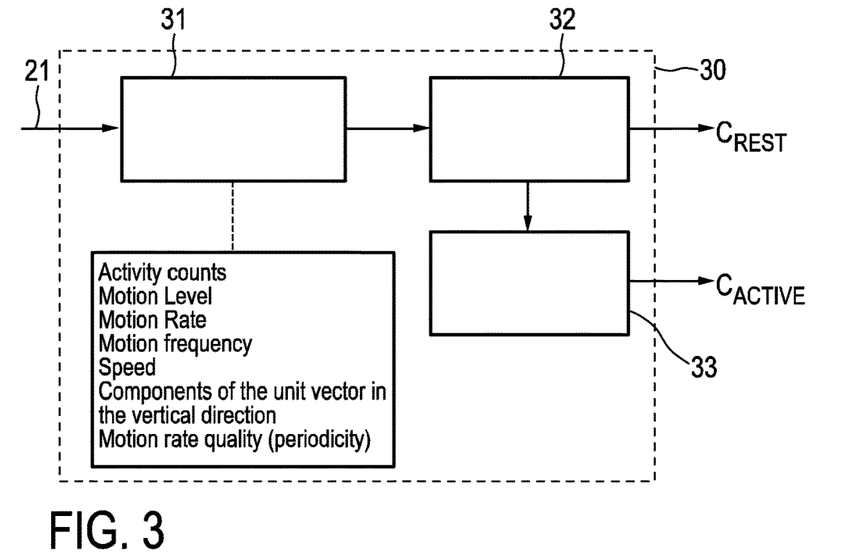
FIG. 3 shows a schematic diagram of an embodiment of a classifier.

A schematic diagram of an embodiment of a classifier 30 is depicted in FIG. 3. In the simplest embodiment the classifier 30 will recognize if an activity is performed or not by the user, i.e. will determine a corresponding indicator, such as rest (no activity) and activity.

The signal recorded with the physical activity monitor 20 can further be used to derive information about movement rate, intensity, speed, energy or signal entropy. These characteristics are useful to develop a machine learning algorithm able to classify activity states such as rest and activity. A review of different techniques to identify and to classify different activities from body-worn sensor data can be found in Preece S J, Goulermas J Y, Kenney L P, Howard D, Meijer K, Crompton R. Activity identification using body-mounted sensors—a review of classification techniques. Physiol Meas. 2009 April; 30(4):R1-33. doi: 10.1088/0967-3334/30/4/R01. Epub 2009 Apr. 2.

Referring again to the exemplary embodiment of the classifier 30 in FIG. 3, the classifier 30 receives the activity signal 21 recorded with the physical activity monitor 20. The classifier includes a feature extractor 31, which calculates movement features from the activity signal 21 such as activity counts measured on a minute-basis (AC); a motion level, i.e., an amplitude of the signal area under the curve (ML); a motion rate (MR, bpm); a motion frequency; a speed of motion; components of the unit vector along the vertical direction (gravity vector) projected in the three sensing axes of the accelerometer (Cx, Cy, Cz); a signal entropy (J); and a motion quality, e.g. an inverse of the signal entropy (MRQuality, e.g. represented as a value in the range from 0 to 1).

Movement features represent the input to a first classifier stage 32, referred to as rest/activity classifier, which determines whether a user is performing physical activity or is being sedentary. The following algorithm can be used to determine the output of the rest/activity classifier:

ModelOutput=$\theta_0+\theta_1$*AC+$\theta_2$*ML+$\theta_3$*Cz+$\theta_4$*MR+ $\theta_5$*MRQuality Probability=$1/(1+e\char`\^(-ModelOutput))$ If Probability<ProbTh$_1$
Output<=$C_{REST}$
Else
Output<=$C_{ACTIVE}$
with the following parameters:
$\theta_1 \ldots_5$=[0.6044, −2.4805, 2.9425, 1.2822, 1.1371, 4.1358];
ProbTh$_1$, decision boundary=0.50;
The classifier 30 can make use of a multi-parametric model which provides a two-stage classification to decide whether the activity belongs to the rest ($C_{REST}$) or the activity ($C_{ACTIVE}$) class, where $C_{REST}$ and $C_{ACTIVE}$ represent the class output of the classifier indicating a condition of rest or activity. In case activity is detected by the first classifier unit 32, a second classifier unit 33, referred to as activity type classifier, is employed to discriminate between types of physical activity. Distinction between walking, walking stairs, running, and cycling can be made by evaluating movement features related to speed of movement and changes in altitude to detect walking up and down stairs. Another example on how this second classifier unit 33 can be built is as a NaiveBayes classifier which describes the probability of activity types given a list of features of the activity signal (as listed above). When the features calculated from the measured activity signal are similar in value to pre-recorded features for a specific activity in a database, the probability that the activity measured by the activity monitor 20 corresponds to the activity identified in the database is large. Thereby, activity types can be classified by the second classifier unit 33. The output $C_{ACTIVE}$ of the classifier 30 then denotes the type of activity.

Furthermore, temporal information related to the duration, onset and termination of physical activity can also be deducted from the classifier output. This information can be further used to characterize HR dynamics such as trends during HR rise at the beginning of an activity, trends in HR recovery after activity termination of HR peaks while the activity is ongoing. These features are then used in combination with VO$_2$max predictive algorithms to estimate cardio-respiratory fitness.

According to whether an activity is performed or not and according to which HR phase is available (e.g. rising HR, steady-state exercise HR, HR recovery) the selector 40 will select the most appropriate HR feature(s) to estimate VO$_2$max for that activity. The most appropriate estimation of VO$_2$max is preferably the one that has shown the lowest Root Mean Squared Error (RMSE) in validation tests (preferably once done in a laboratory in advance).

According to an embodiment a VO$_2$max estimation model is chosen from among a larger number of HR feature based models. For example, if the activity counts are below 1000, the HR rest (e.g. HR rest median) or HRV (e.g. SDNN; standard deviation of NN intervals) regression models are used to estimate VO$_2$max. If the activity counts are between 1000 and 5000 for at least 1 min or more, a regression model based on exercise HR (e.g. HR/counts) is used; if the classifier recognizes at least 30 s of activity recovery, HR recovery (e.g. slope or delta) is used and so on.

In the following examples of regression models based on several different HR features are shown:
i) VO$_2$max [L/kg/min]=69.9243−0.40637×HRrest median
TRAINING
bias=−9.77e−015
rmse=5.8772%
% std=0.1428%
% mean=−0.022043%
% see=0.035767
VALIDATION
bias=1.6395
rmse=7.5044%
% std=0.17599%
% mean=0.020929%
% see=0.040603
ii) VO$_2$max [L/kg/min]=50.1855−1.3398×STD HR during rest (SDNN)
TRAINING
bias=−6.2172e−015 rmse=5.9303%
% std=0.14409%
% mean=−0.021243%
% see=0.034673
VALIDATION
bias=1.5481
rmse=6.2864%
% std=0.14643%
% mean=0.018633%
% see=0.032297
iii) $VO_2max$ [L/kg/min]=43.4858−0.0090276×Rise Tau exponential fit
TRAINING
bias=−7.6383e−015
rmse=6.2464%
% std=0.15176%
% mean=−0.02538%
% see=0.03968
VALIDATION
bias=0.27444
rmse=7.0794%
% std=0.16974%
% mean=−0.015193%
% see=0.04097
iv) $VO_2max$ [L/kg/min]=29.958+0.4424×Recovery DeltaHR over 30 sec
TRAINING
bias=−3.7303e−015
rmse=5.9601%
% std=0.14481%
% mean=−0.022976%
% see=0.037613
VALIDATION
bias=1.8209
rmse=7.2645%
% std=0.16901%
% mean=0.021432%
% see=0.040426
v) $VO_2max$ [L/kg/min]=34.0319−11.718×Recovery slope
TRAINING
bias=5.862e−015
rmse=5.9956%
% std=0.14567%
% mean=−0.023327%
% see=0.037605
VALIDATION
bias=1.5238
rmse=7.7082%
% std=0.18159%
% mean=0.012476%
% see=0.044786
vi) $VO_2max$ [L/kg/min]=66.8135−6.0392×sex−3684.1417×FitnessIX→ratio HR/Counts for walk/run (if walking and running HR and activity counts are available)
Stepwise MLR Training
bias=1.7764e−016
rmse=4.8545%
% std=0.11795%
% mean=−0.015754%
% see=0.031514
Stepwise MLR VALIDATION
bias=1.9627
rmse=5.5032%
% std=0.12336%
% mean=0.038283%
% see=0.02918

These number report the performance of the models.

Figure 4:
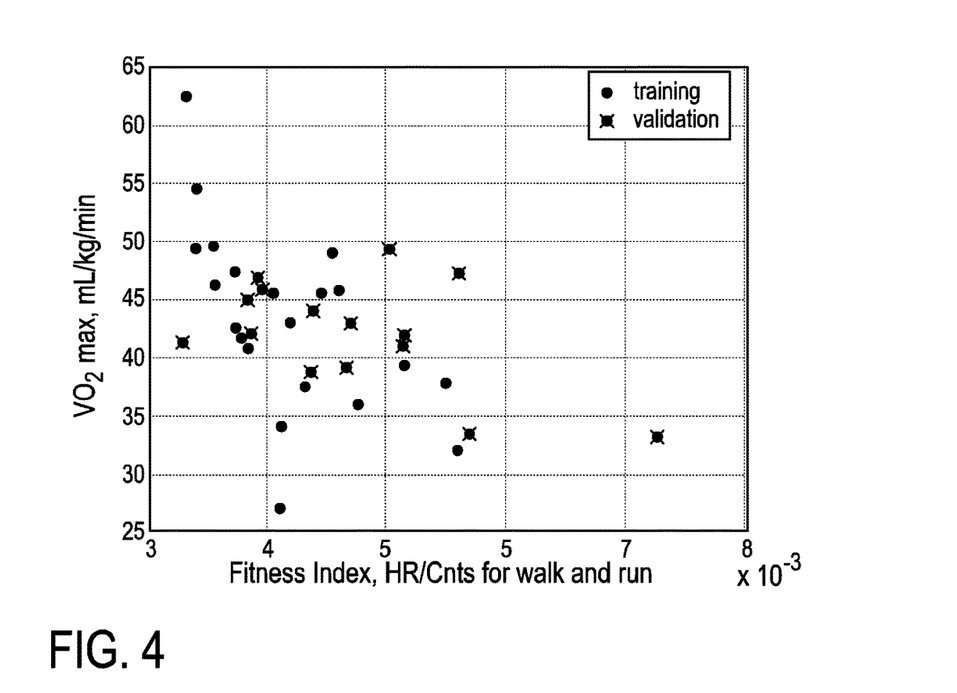
FIG. 4 shows a diagram illustrating the correlation between $VO_2$max and HR/Counts during walking and running.

FIG. 4 depicts a diagram illustrating the correlation between $VO_2max$ and HR/Counts during walking and running. It illustrates how the model HR/counts performs in estimating $VO_2max$.

Figure 5:
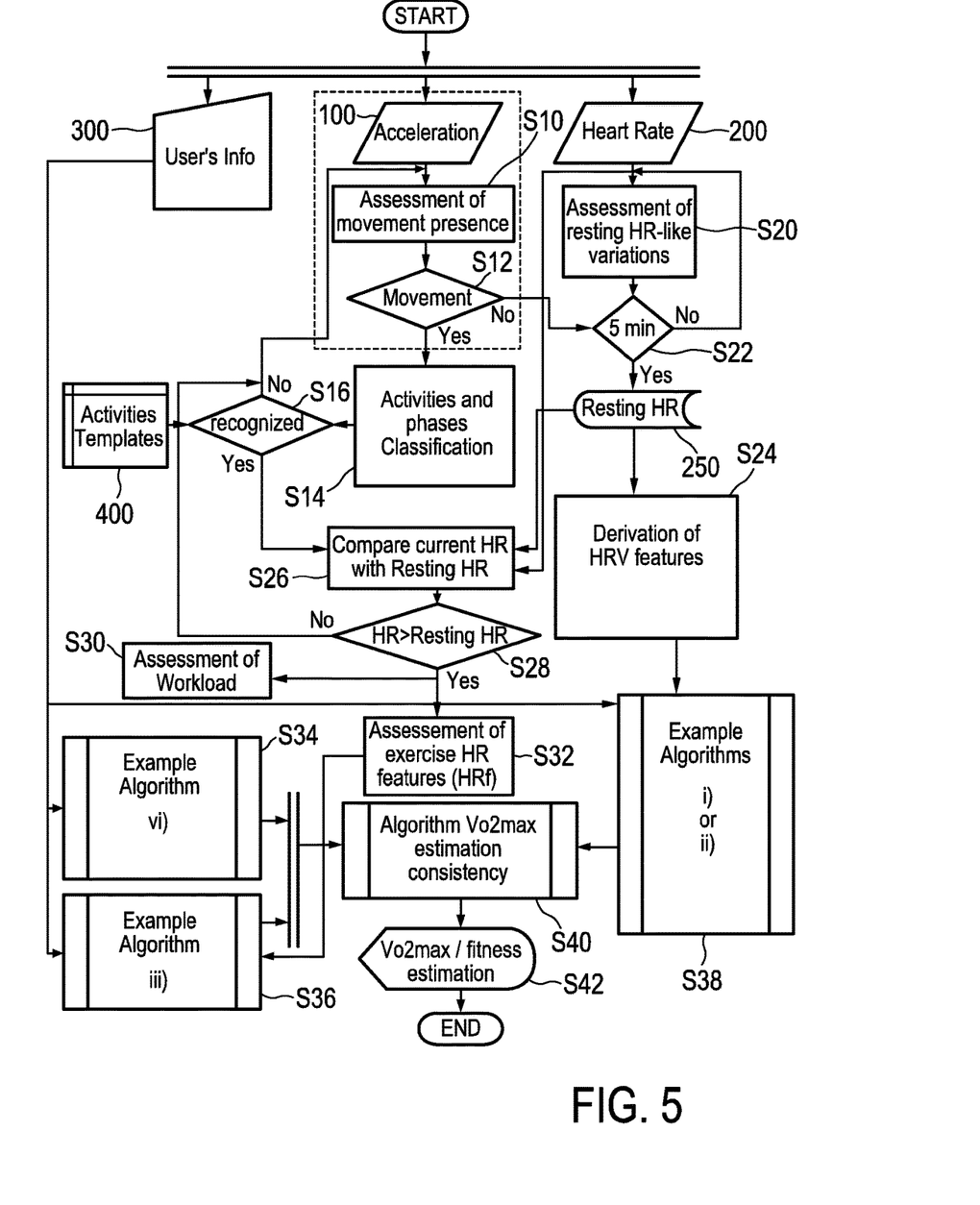
FIG. 5 shows a flow chart of an embodiment of a method according to the present invention.

FIG. 5 shows a flow chart of an embodiment of a method according to the present invention. This algorithm chooses the $VO_2max$ estimation generated by the predictive model with the lowest validation RMSE, based on the data available. A predictive model is an algorithm which compares the lab errors of the models based on all the HR features available. For example if three features have been detected model 1→HR feature 1 Error=3
model 2→HR feature 2 Error=3.5
model 3→HR feature 3 Error=1 then the system chooses the $VO_2max$ estimated by model 3.

For instance it could happen that only part of the HR recovery data is available so that the heart rate feature "Recovery slope" is available. Then, the $VO_2max$ estimation is based on HR Recovery slope model (RMSE=7.7). But in case that also resting data is available, STD HR during rest (SDNN) can be used. This will be the displayed $VO_2max$ prediction, since its RMSE is 6.3 and therefore lower than for the HR Recovery model.

In a first step S10 an assessment of the presence of movement is made based on acceleration signal 100. If movement is present, as checked in step S12, a classification of activities and heart rate phases is made in step S14, i.e. the type of activity (such as walking, running, raising, steady-state, recovery, cycling, etc.) is detected. If no certain type of activity is recognized, as checked in step S16 by use of activities templates 400, the algorithm returns to step S10.

In a parallel path of processing resting HR-like variations are assessed based on the heart rate signal 200 in step S20. If there is no movement detected, as checked in step S12 and if 5 min have passed, as checked in step S22, a resting HR 250 is detected. Otherwise, the algorithm returns to step S20. In step S24 a derivation of HRV features (in the time domain and/or frequency domain; non-linear) is then made.

If a certain type of activity is recognized, as checked in step S16, the current HR 200 is compared with the resting HR 250 in step S26. Subsequently, it is checked in step S28, if the current HR is higher than the resting HR. If this is not the case, the algorithm returns to step S16. Otherwise, an assessment of workload (e.g. speed) is made in step S30 and/or an assessment of exercise HR features (HRf) is made in step S32. An example algorithm S34 for step S30, which in addition uses user information 300 (e.g. age, gender, weight of the user) is indicated above as example vi). An example algorithm S36 for step S32, which also uses user information 300, is indicated above as example iii). Example algorithms S38 for step S24, which also use user information 300, are indicated above as examples i) and ii).

Finally, in step S40 the consistency of the various estimations in steps S34, S36, S38 is made, preferably based on the lowest RMSE, and the most consistent estimation result is output in step S42.

Generally, any HR monitor can be used in combination with any activity monitor. A useful embodiment comprises an optical HR sensor that is worn by the user on his body (for instance at the wrist or around the chest). An accelerometer is also worn by the user on his body (this could be at the same location or at a different location).

In an embodiment, when the accelerometer detects acceleration (and, thus, movement), information from the HR sensor is used by the classifier to discriminate which type of activity is performed by the user. Once a type of activity useful for the fitness estimation is recognized (such as walking, running, cycling etc.) the workload (e.g. speed, or the speed and incline, etc.) of this activity is estimated from the acceleration data. At the same time HR derived parameters coming from peak HR are used together with user's characteristics to estimate the user's $VO_2max$. Once the accelerometer does no longer detect movement, HR recovery parameters are extracted to make a further estimate of the user's $VO_2max$. In case the accelerometer does not detect any movement and the HR of the user is at rest, HRV statistical measures together with user's information are used to estimate the user's $VO_2max$.

In an embodiment the consistency between these $VO_2max$ estimations is evaluated (e.g. based on the lowest RMSE), which will select the most consistent estimation, increasing the accuracy of the estimation.

The present invention can be used in various applications. A first field of application is in sports where $VO_2max$ estimation is important to assess the capacity of the athlete to improve and to track the effect of an aerobic training. A second field of application is the fitness industry, such as gyms, fitness centres etc. A third field of application is clinical since cardiorespiratory and cardiovascular function is a very important diagnostic and prognostic information in several clinical populations. Moreover, cardiovascular fitness monitoring is very important in order to assess the improvements of patients recovering from a heart event, such as a heart attack. Finally, self monitoring of $VO_2max$ is important since it gives information of the cardiovascular fitness, which is valuable information in asymptomatic adults.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for estimating a maximal oxygen uptake ($VO_2max$) of a person, the device comprising:
   a heart rate monitor that acquires a heart rate signal including information about the heart rate of the person;
   an activity monitor that acquires an activity signal indicative of physical activity of the person; and
   a processor operably coupled with memory, the heart rate monitor, and the activity monitory, the processor being configured to cause instructions to execute to:
   classify an activity of the person based on the activity signal into cycling, walking, running, steady recovery, or no activity;
   identify one or more heart rate features that are available from the heart rate signal;
   select, based on the classification of the activity and the identified heart rate features, one or more $VO_2max$ estimation models from a plurality of heart rate feature-based $VO_2max$ estimation models stored in the memory;
   select, for each selected $VO_2max$ estimation model of the one or more selected $VO_2max$ estimation models, an available heart rate feature that is based on the acquired heart rate signal;
   estimate the $VO_2max$ of the person based on one or more selected available heart rate features and the one or more selected $VO_2max$ estimation models; and
   output, on a display, information indicative of the estimated $VO_2max$.

2. The device as claimed in claim 1, wherein selecting the available heart rate feature obtained from the acquired heart rate signal comprises selecting the available heart rate feature from the group of heart rate features comprising heart rate recovery, peak heart rate, heart rate variability, heart rate rise, resting heart rate.

3. The device as claimed in claim 1, wherein selecting the available heart rate feature obtained from the acquired heart rate signal comprises selecting the available heart rate feature based on which heart rate phase is currently present.

4. The device as claimed in claim 1, wherein estimating the $VO_2max$ comprises estimating the $VO_2max$ of the person based on the one or more selected available heart rate features and user information about the person including one or more of age, gender, weight, height, body mass index of the person received via an interface.

5. The device as claimed in claim 1, wherein selecting the available heart rate feature is based on a root mean square error associated with at least one model of the one or more selected $VO_2max$ estimation models.

6. The device of claim 1, wherein said activity monitor includes an accelerometer for acquiring an acceleration signal indicative of acceleration of at least part of the body of the person as activity signal.

7. The device of claim 1, wherein said heart rate monitor includes a photo-plethysmography or optical sensor.

8. A method for estimating a maximal oxygen uptake ($VO_2max$) of a person using one or more processors, the method comprising:
   acquiring, by one or more of the processors from a heart rate monitor worn on the person's body, a heart rate signal that includes information indicative of physical activity of the person;
   acquiring, by one or more of the processors from an accelerometer worn on the person's body, an activity signal indicative of physical activity of the person;
   classifying an activity of the person based on the acquired activity signal into cycling, walking, running, steady recovery, or no activity;
   identifying one or more heart rate features that are available from the heart rate signal;

selecting, based on the classification of the activity and the identified heart rate features, one or more $VO_2max$ estimation models from a plurality of heart rate feature-based $VO_2max$ estimation models stored in the memory;

selecting, for each selected $VO_2max$ estimation model of the one or more selected $VO_2max$ estimation models, an available heart rate feature that is based on the acquired heart rate signal;

estimating the $VO_2max$ of the person based on one or more selected available heart rate features and the one or more selected $VO_2max$ estimation models; and outputting, on an output component, information indicative of the estimated $VO_2max$.

9. The method of claim 8, wherein selecting the available heart rate feature is based on a root mean square error associated with at least one model of the one or more selected $VO_2max$ estimation models.

10. The method of claim 8, wherein selecting the available heart rate feature obtained from the acquired heart rate signal comprises selecting the available heart rate feature from the group of heart rate features comprising heart rate recovery, peak heart rate, heart rate variability, heart rate rise, resting heart rate.

11. The method of claim 8, wherein said heart rate monitor includes a photo-plethysmography.

12. The method of claim 8, wherein estimating the $VO_2max$ comprises estimating the $VO_2max$ of the person based on the one or more selected available heart rate features and user information about the person including one or more of age, gender, weight, height, body mass index of the person received via an interface.

13. The method of claim 8, wherein selecting the available heart rate feature obtained from the acquired heart rate signal comprises selecting the available heart rate feature based on which heart rate phase is currently present.

14. The method of claim 8, wherein said heart rate monitor includes an optical sensor.

15. At least one non-transitory computer-readable medium comprising instructions that, in response to execution of the instructions by one or more processors, cause the one or more processors to estimate a maximal oxygen uptake ($VO_2max$) of a person by performing the following operations:

acquiring, by one or more of the processors from a heart rate monitor worn on the person's body, a heart rate signal that includes information indicative of physical activity of the person;

acquiring, by one or more of the processors from an accelerometer worn on the person's body, an activity signal indicative of physical activity of the person;

classifying an activity of the person based on the acquired activity signal into cycling, walking, running, steady recovery, or no activity;

identifying one or more heart rate features that are available from the heart rate signal;

selecting, based on the classification of the activity and the identified heart rate features, one or more $VO_2max$ estimation models from a plurality of heart rate feature-based $VO_2max$ estimation models stored in the memory;

selecting, for each selected $VO_2max$ estimation model of the one or more selected $VO_2max$ estimation models, an available heart rate feature that is based on the acquired heart rate signal;

estimating the $VO_2max$ of the person based on one or more selected available heart rate features and the one or more selected $VO_2max$ estimation models; and outputting, on an output component, information indicative of the estimated $VO_2max$.

16. The at least one non-transitory computer-readable medium of claim 15, wherein selecting the available heart rate feature is based on a root mean square error associated with at least one model of the one or more selected $VO_2max$ estimation models.

17. The at least one non-transitory computer-readable medium of claim 15, wherein selecting the available heart rate feature obtained from the acquired heart rate signal comprises selecting the available heart rate feature from the group of heart rate features comprising heart rate recovery, peak heart rate, heart rate variability, heart rate rise, resting heart rate.

18. The at least one non-transitory computer-readable medium of claim 15, wherein said heart rate monitor includes a photo-plethysmography or optical sensor.

19. The at least one non-transitory computer-readable medium of claim 15, wherein estimating the $VO_2max$ comprises estimating the $VO_2max$ of the person based on the one or more selected available heart rate features and user information about the person including one or more of age, gender, weight, height, body mass index of the person received via an interface.

20. The at least one non-transitory computer-readable medium of claim 15, wherein selecting the available heart rate feature obtained from the acquired heart rate signal comprises selecting the available heart rate feature based on which heart rate phase is currently present.

* * * * *